United States Patent [19]

Schmitthenner

[11] Patent Number: 4,758,678

[45] Date of Patent: Jul. 19, 1988

[54] PREPARATION OF 7-(2,3-EPOXYPROPOXY)FLAVONE

[75] Inventor: Hans F. Schmitthenner, Honeoye Falls, N.Y.

[73] Assignee: Pennwalt Corporation, Philadelphia, Pa.

[21] Appl. No.: 887,756

[22] Filed: Jul. 18, 1986

[51] Int. Cl.$^4$ .......................................... C07D 311/30
[52] U.S. Cl. .................................................. 549/403
[58] Field of Search ....................................... 549/403

[56] References Cited

U.S. PATENT DOCUMENTS

| | | | |
|---|---|---|---|
| 3,419,578 | 12/1968 | Fitzmaurice et al. | 549/402 |
| 3,862,175 | 1/1975 | Fitzmaurice et al. | 549/402 |
| 4,093,631 | 6/1978 | Gardner | 549/408 |
| 4,391,821 | 7/1983 | Korbonits et al. | 514/456 |

Primary Examiner—Nicky Chan

[57] ABSTRACT 7-(2,3-Epoxypropoxy)flavone is prepared by the reaction of 7-hydroxyflavone with an epihalohydrin in the presence of a weak base and acetonitrile.

3 Claims, No Drawings

PREPARATION OF 7-(2,3-EPOXYPROPOXY)FLAVONE

This invention relates to a process for the preparation of 7-(2,3-epoxypropoxy)flavone via the reaction of 7-hydroxyflavone and an epihalohydrin.

BACKGROUND 7-2,3-Epoxypropoxy)flavone is useful as an intermediate for the preparation of 7-[3-(alkylamino)-2-hydroxypropoxy]flavones, which aminated flavones are disclosed in U.S. Pat. No. 4,495,198 to be particularly useful as antihypertensives. This patent shows the preparation of 7-(2,3-epoxypropoxy)flavone in low yields by reaction of 7-hydroxyflavone and an epihalohydrin in the presence of either sodium hydroxide and ethanol (59% yield) or potassium carbonate and acetone (68% yield after refluxing for 2 days).

BRIEF SUMMARY OF THE INVENTION

The present invention relates to a process for the preparation of 7-(2,3-epoxypropoxy)flavone wherein 7-hydroxyflavone is contacted with an epihalohydrin (epichlorohydrin or epibromohydrin) in the presence of a weak base (sodium carbonate or potassium carbonate) and acetonitrile.

DETAILED DESCRIPTION

It has now been found that the use of acetonitrile as a solvent, instead of the protic solvent, ethanol, or the aprotic solvent, acetone, results in much higher yields (typically 87–90%) of the desired product, as well as reducing reaction times and dimer by-products.

Preferably, an excess of the epihalohydrin is used to minimize flavone dimer formation. Generally, 2 to 4 molar equivalents of epibromohydrin (preferably 2 to 2.5) or 10 to 12 molar equivalents of epichlorohydrin are employed.

The reaction is normally carried out at an elevated temperature of at least about 70° C. to achieve a reasonable rate and to avoid significant dimer formation. Temperatures above about 80° C. are generally avoided since higher temperatures tend to result in more by-products and reduced yields. The preferred range is about 70°–75° C., most preferably 75° C. The reaction duration normally ranges from 8 to 24 hours, more typically about 10 to 16 hours, depending on the other process parameters.

From about 2 to about 5 molar equivalents of the weak base, per mole of the 7-hydroxyflavone, is a normal range for an efficient reaction, with about 2 molar equivalents being preferred. More than 5 equivalents works well but is unnecessary. The preferred weak base is potassium carbonate.

The acetonitrile is normally used in a range of about 15 to 30 volumes (in ml) per weight (in grams) of the 7-hydroxyflavone, preferably about 17.5 to 20 volumes. The use of dilute conditions assists in suppressing dimer formation.

The 7-(2,3-epoxypropoxy)flavone product can be isolated using any suitable method, such as filtration followed by concentration of the filtrate. Generally, it is preferred to slurry the product in a lower alcohol such as isopropanol before the product is isolated. Acetonitrile can also be used to slurry the product. The slurrying step results in a superior yield compared to standard recrystallization methods and provides better purity over direct concentration to dryness.

The 7-(2,3-epoxypropoxy)flavone can be converted to 7-[3-(alkylamino)-2-hydroxypropoxy]flavones by reaction with an amine as described in said U.S. Pat. No. 4,495,198, the specification of which is incorporated herein by reference.

The invention is further illustrated by the following examples in which all the parts and percentages are by weight unless otherwise indicated.

EXAMPLE 1

Twenty grams (0.084 mol) of 7-hydroxyflavone are mixed with 400 ml of acetonitrile, and 27.6 g (0.20 mol) of epibromohydrin and 23.2 g (0.168 mol) of potassium carbonate are added to this mixture, followed by heating at 70°–75° C. for 16 hours with brisk stirring. The progress of the reaction is monitored by tlc (thin layer chromatography), 25% ether in methylene chloride, visualized by short UV. The hot reaction mixture is filtered and the solid obtained is rinsed with 50ml warm acetonitrile. The clear light yellow filtrate is concentrated under reduced pressure to a semisolid residue which is slurried under 100–150 ml of isopropyl alcohol, filtered, and washed with 50 ml of isopropyl alcohol. The off-white solid obtained is air dried and thereafter subjected to vacuum at 50° C.; yield is 22.2 g (0.0754 mol), 90%; m.p. 127°–130° C. A chromatographed and recrystallized sample has a melting point of 130°–133° C.

Alternatively, the clear light yellow filtrate concentrated to a semisolid residue as described above can be slurried with acetonitrile rather than isopropyl alcohol. Carrying out the slurrying operation with acetronitrile (100–150 ml) provides an 87% yield in two crops.

EXAMPLE 2

Twenty grams (0.084 mol) of 7-hydroxyflavone are mixed with 350 ml of acetonitrile, and 77.7 g (0.84 mol) of epichlorohydrin and 23.2 g (0.168 mol) of potassium carbonate are added to this mixture, followed by heating at 75° C. for 16 hours with brisk stirring. The progress of the reaction is monitored by tlc, 25% ether in methylene chloride, visualized by short UV. The hot reaction mixture is filtered and the solid obtained is rinsed with 50 ml of warm (approx. 50° C.) acetonitrile. The clear light yellow filtrate obtained is concentrated under reduced pressure to a semisolid residue which is slurried with 100–150 ml of isopropyl alcohol, filtered, and washed with 50 ml isopropyl alcohol. The off-white solid product obtained is air dried and then subjected to vacuum at 50° C.; yield is 21.5 g (0.073 mol), 87%; m.p. 126°–129° C.; m.p. of chromatographed and recrystallized sample is 130°–133° C.

What is claimed is:

1. A process for the preparation of 7-(2,3-epoxypropoxy)flavone which comprises (a) contacting 7-hydroxyflavone with an epihalohydrin selected from epibromohydrin and epichlorohydrin in the presence of acetonitrile and a weak base selected from sodium carbonate and potassium carbonate, and (b) isolating 7-(2,3-epoxypropoxy)flavone from the resultant reaction mixture.

2. The process of claim 1 wherein the weak base consists of about two moles of potassium carbonate per mole of 7-hydroxyflavone.

3. The process of claim 2 wherein step (a) is carried out at a temperature of from about 70° C. to about 75° C.

* * * * *